United States Patent [19]

Himmler

[11] 3,961,525

[45] June 8, 1976

[54] METHOD OF AND DEVICE FOR TESTING THE FATIGUE STRENGTH OF ROTORS, ESPECIALLY DISC WHEELS, ESPECIALLY THOSE FOR MOTOR VEHICLES

[75] Inventor: Gunther Himmler, Darmstadt, Germany

[73] Assignee: Gebr. Hofmann KG, Darmstadt, Germany

[22] Filed: Sept. 13, 1974

[21] Appl. No.: 505,835

[30] Foreign Application Priority Data
Dec. 17, 1973    Germany............................. 2362559

[52] U.S. Cl. ................................................. 73/91
[51] Int. Cl.² .......................................... G01N 3/32
[58] Field of Search............ 73/100, 91, 67.3, 71.5 R

[56] References Cited
UNITED STATES PATENTS
2,953,018    9/1960    Volmer................................. 73/91
FOREIGN PATENTS OR APPLICATIONS
22,483    4/1956    Germany......................... 73/71.5 R

*Primary Examiner*—James J. Gill
*Assistant Examiner*—Anthony V. Ciarlante
*Attorney, Agent, or Firm*—Cushman, Darby & Cushman

[57] ABSTRACT

A method and apparatus for testing the fatigue strength of a stationary rotor whereby the rotor is clamped to an exciter rod and opposite transverse forces applied to the rod at different distances from the point of clamping by rotating weight to produce substantially no net radial forces.

11 Claims, 1 Drawing Figure

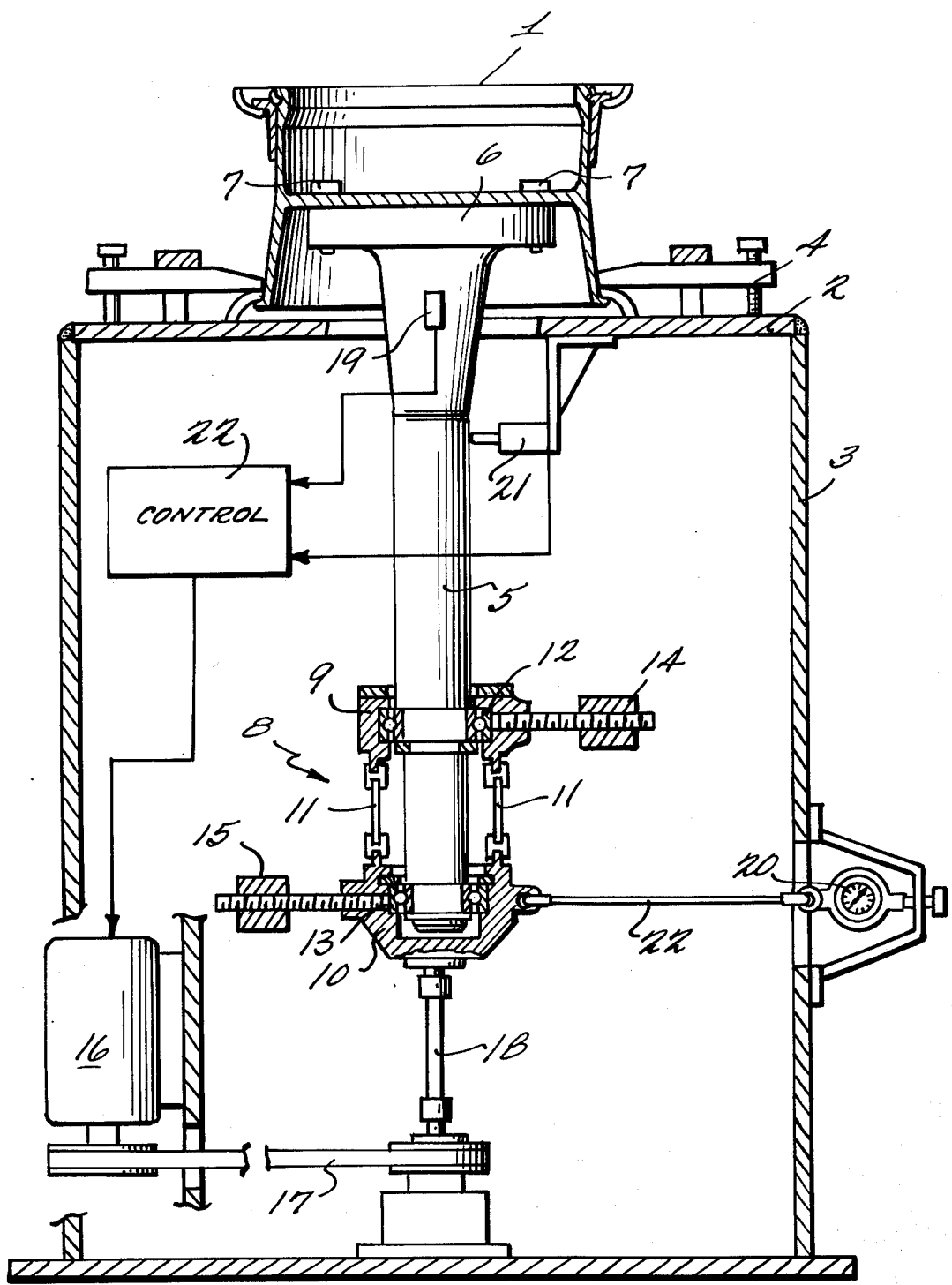

METHOD OF AND DEVICE FOR TESTING THE FATIGUE STRENGTH OF ROTORS, ESPECIALLY DISC WHEELS, ESPECIALLY THOSE FOR MOTOR VEHICLES

The invention relates to a method of testing the fatigue strength of rotors, especially disc wheels, with which the rotor is kept stationary, and with which a loading is introduced into the rotor by means of an exciter rod on which transverse forces act, as well as to a device for testing the fatigue strength of rotors, especially disc wheels, with a clamping device keeping the rotor stationary, and an exciter one end of which may be connected to the rotor and the other end of which carries a rotatable exciter head by means of which transverse forces acting on the exciter rod can be produced.

In modern vehicles not only tires and travel gears must be resistant to high stress, but also the disc wheels on which the tires are mounted. With a view to the travel gear dynamics and the cost of material it is desired to keep the weight of the disc wheel as low as possible and to obtain a high degree of rigidity and capacitance at the same time. When judging these requirements, the operating safety must, however, be considered as the most important factor.

Due to the complicated geometric shape of the wheel and the varying introduction of force by the tire, the frictional connection at the individual points of the disc wheel varies and the collective tensions occurring during driving are different for each point. As it is almost impossible to carry out a mathematical calculation of the stress functions for the individual system points and as it is difficult to select the right parameters, a mathematical calculation of the disc wheel is hardly feasible. The shape of the disc wheel is therefore determined on the testing machine in consideration of the operating conditions. Since the stress occurs periodically, fatigue tests are carried out including rotating bending tests.

Testing machines for disc wheels have become known (German Pat. No. 1,000,168), with which a force or a weight produces a static load and the disc wheel rotates together with the bending shaft. With the known device the revolving fatigue strength is impressed on the disc wheel through a load arm to which a weight is attached and which rotates together with the disc wheel. From the German Publication of the Examined Application No. 1,063,403 also a method and a device of the kind described in the beginning are known. The disc wheel to be tested is in this case fixed and connected to an exciter rod which is also at rest. The stress is caused by a rotary centrifugal force of unbalance. This known fatigue strength testing machine thus functions according to the principle of the generation of centrifugal force of unbalance.

With the device described in the German Pat. No. 1,000,168 the disc wheel to be tested cannot be watched continuously so that it is hardly or not at all possible to determine the development and course of a crack. Besides, a larger drive energy is required with this device as the disc wheel and the clamping flange must rotate together with the exciter rod.

With the fatigue strength testing machine according to the German Publication of the Examined Application No. 1,063,403 a continuous observation is feasible and the drive energy is relatively small. However, besides the bending strain an inevitably existing additional radial strain becomes effective which cannot be avoided and which can be so large that the whole measuring result becomes inaccurate.

In the case of a testing moment determined in advance or desired, the force to be produced depends on the length of the exciter rod. But as the rod cannot have an optional length because of inherent frequencies and for constructional reasons, the test force may arrive at values which are unlike those occurring during the traveling operation so that due to its amount the number of cycles to failure of the disc wheel may be reduced decisively.

It is the object of the invention to introduce, with a method and a device for testing the fatigue strength of rotors, a testing moment in such a way that the radial force load can be reduced to zero so that bending moments arise exclusively and either no radial forces or only such radial forces, the amount of which can be adjusted, are introduced together with such moments.

This object is achieved according to the invention with a method of the kind described in the beginning in that the transverse forces act on the exciter rod from different distances from the clamping surface of the rotor.

With a device of the kind described in the beginning, the object is achieved according to the invention in that, for producing the transverse forces acting on the exciter rod, the exciter head is provided with rotary weights rotating in planes which lie at different distances from the clamping surface of the rotor.

For producing the transverse forces a force couple may act on the exciter rod of the testing machine. The transverse forces caused by the force couple can in this case be displaced by 180° with respect to each other so that it becomes possible to introduce moments free from radial load. Besides, the invention allows an adjustment of the force couple in such a manner that the disc wheel which is free from radial load, can be subjected to radial load in a continuous procedure.

The distances between the weights and the axis of rotation of the exciter head and the angular displacement of the weights with respect to each other may be adjustable. The weights may be interconnected by means of flexible couplings or the like, in order to reduce to a minimum the reciprocal influence of the centrifugal forces of the weights. Preferably two weights are provided on the exciter head. The weights may be angularly displaced with respect to each other so that with an angular displacement of 180° of the two weights an introduction of moments free of radial load can be obtained and that with identical angular positions a maximum transverse force is obtained. Drive of the exciter head may be effected by a motor through flexible means.

The bending moment introduced into the disc wheel through the exciter rod may be measured with the aid of strain gauges attached to the exciter rod, preferably at the upper half of it, and indicated on a measuring electronic device. Also the number of rotations of the rotary weights can be controllable, dependent on the deflection of the exciter rod. In this way, the produced bending moment can be kept constant.

With the aid of the invention it is possible to reduce the stress of the disc wheel to a rotationary bending moment. According to theoretical reflections it is sufficient if, as a basis for the method of testing the disc wheel, the stress of the disc wheel is reduced to a rotationary bending moment. Of course, there is also the possibility of adjusting the weights in order to have the disc wheel which is free of radial load, subjected to radial load for the test.

On the basis of the enclosed FIGURE, the invention will now be explained in detail with a construction example. The FIGURE shows a lateral view of the device according to the invention, with a section through the center axle of the device.

A disc wheel 1 is clamped to a machine table 2 of an overall housing 3, preferably by means of clamping shoes 4. An exciter rod 5 designed as bending rod the upper end of which is forged out as flange 6, is preferably connected to the disc wheel 1 according to the diameter of the bolthole circle by means of conventional wheel studs 7. At the other end of the bending rod 5 an exciter head 8 is provided. The exciter head 8 consists of an upper part 9 and a lower part 10 which are interconnected by means of preferably flexible couplings 11 which prevent a radial magnetic flux between parts 9 and 10. Parts 9 and 10 are pivoted on the bending rod by means of the ball bearing 12 and 13 respectively and are provided with the radially adjustable weights 14 and 15, respectively. Parts 9 and 10 with the weights 14 and 15 may furthermore be turned by 180° with respect to each other in a way not shown in the FIGURE. The exciter head 8 may be driven by a motor 16. Motor 16 and exciter head 8 may be connected by a belt drive 17 or similar transmission means or by a telescopic cardan shaft 18 which varies as the centrifugal force causes a deflection of the bending rod 5.

Preferably within the clamping range of the disc wheel 1 strain gauges 19 are provided on the bending rod 5, especially four of them, arranged on the circumference displaced by 90° each, the geometric signals of which are added so that the maximum value is always present. These strain gauges measure the introduced bending moment, and the measured values are indicated on a conventional electronics device not shown in the FIGURE. The calibration of the value is effected in a known way by means of a calibration system 20 during standstill of the machine. The connection 22 between the calibration system 20 and the exciter head 8 is undone after the adjustment.

The deflection of the bending rod 5 is preferably measured by means of contact-free mechanic-electrical vibration transducers 21, whereby especially two transducers are used which are arranged on the circumference displaced by 90° with respect to each other, so that even a path curve of the deflection, e.g., an ellipse, can be determined. The measured values of the strain gauges 19 and the transducers 21 are fed to a conventional automatic control circuit (not shown in the FIGURE) which examines and regulates the introduced torque in any suitable fashion, e.g., varying the speed of rotation of weights 14 and 15.

When carrying out the testing, the disc wheel 1 which is clamped to the machine table 2, is loaded with a bending moment through the bending rod 5. The motor 16 is put into rotation and this rotary motion is transmitted to the exciter head through the cardan shaft 8. During the rotation of the exciter head 8 the weights 14 and 15 exert transverse forces on the bending rod 5 on account of their centrifugal forces. These transverse forces can be equally large, whereby the weights 14 and 15 are, e.g., equally large and the distances between the weights and the axis of rotation of the exciter head are equal, too. Also, the angular displacement can be 180° as shown in the FIGURE. In that case moments free of radial force can be introduced into the disc wheel 1.

The alternating bending load introduced into the disc wheel causes, after a certain number of load alternations, cracks in the material of the disc wheel, which become larger and larger until a fatigue fracture occurs. As the cross section of the material is reduced due to the formation of the crack, the material becomes less rigid and thus the deflection of the exciter head increases. With a certain maximum deflection of the exciter head the machine can be automatically shut down by actuation of a switch (not shown in the FIGURE).

In order to keep the produced bending moment constant, the deflection of the bending rod 5 and the modification of the bending moment are measured by means of the vibration transducers 21 and the strain gauges 19. In an automatic control system 22 the actual value and the theoretical value can be compared with each other and if there is a differential tension the speed of revolutions of the exciter head 8 is reduced until the prescribed or desired bending moment has been obtained again.

When calibrating the electronics which evaluates the measuring values of the strain gauges 19, the linear reduction factor between the bending moment at the clamping point and the bending moment at the point of attachment of the strain gauges 19 is considered as well as the geometric and material-dependent quality of the exciter head and of the strain gauges and the transfer factor of the measuring electronics.

Many changes and modifications in the above-described embodiment of the invention can, of course, be carried out without departing from the scope thereof. Accordingly, that scope is intended to be limited only by the scope of the appended claims.

What is claimed is:

1. A method of testing the fatigue strength of a stationary rotor comprising the steps of:
   clamping the rotor on an exciter rod; and
   rotating rotary weights in parallel planes lying at different distances from said clamping point to apply equal and opposite transverse forces to said rod so as to reduce the net radial forces substantially to zero.

2. A method as in claim 1, including detecting the deflection of said rod and varying the speed of rotation of said weights as a function of the deflection of said rod.

3. In an apparatus for testing the fatigue strength of a rotor having a clamping means for mounting the rotor, an exciter rod connected at one end to the rotor and the other end of which carries a rotatable exciter head by means of which transverse forces acting on the exciter rod can be produced, the improvement comprising rotary weights mounted 180° apart on said exciter head and rotating in planes which lie at different distances from the clamping surface of the rotor for producing the transverse forces acting on the exciter rod.

4. In an apparatus according to claim 3, the further improvement including means for adjusting the distances between the weights and the axis of rotation of the exciter head.

5. In an apparatus according to claim 3, the further improvement comprising flexible coupling means interconnecting the weights.

6. In an apparatus according to claim 3, the improvement wherein two weights are mounted on said exciter head.

7. In an apparatus according to claim 3, the improvement wherein the weights are dimensioned so that the resultant force produced by them is zero.

8. In an apparatus according to claim 7, the improvement furhter including vibration transducers for picking up the deflection of the exciter rod.

9. In an apparatus according to claim 3, the further improvement comprising means for controlling the number of revolutions of the rotary weights as a function of deflection of the exciter rod.

10. In an apparatus according to claim 9, the improvement further including strain gauges for measuring the bending moment at the exciter rod.

11. In an apparatus according to claim 9, the improvement including automatic control system for comparing the tensions supplied by the strain gauges and the vibration transducers and varying the number of rotations of the exciter head in the event of a difference of tension so that a constant bending moment is introduced into the rotor.

* * * * *